United States Patent [19]

Anderson et al.

[11] Patent Number: 5,420,336
[45] Date of Patent: May 30, 1995

[54] CATALYST RECOVERY AND DIALKYL ESTER SYNTHESIS

[75] Inventors: Howard W. Anderson, Hockessin, Del.; James E. Matush, Victoria, Tex.; Brent G. Sparks, Singapore, Singapore; Eugene D. Wilhoit, Victoria, Tex.

[73] Assignee: E. I. Du Pont de Nemours and Company, Wilmington, Del.

[21] Appl. No.: 333,339
[22] Filed: Nov. 2, 1994
[51] Int. Cl.⁶ .............................................. C07C 67/03
[52] U.S. Cl. .................................. 560/204; 560/191; 562/528; 502/152; 502/353
[58] Field of Search ...................... 560/190, 191, 204; 502/353, 152; 562/528

[56] References Cited

U.S. PATENT DOCUMENTS

| | | | |
|---|---|---|---|
| 3,564,051 | 2/1971 | Haarer et al. | 260/531 |
| 4,316,775 | 2/1982 | Nash | 203/43 |
| 4,375,552 | 3/1983 | Kuceski | 560/204 |

Primary Examiner—José G. Dees
Assistant Examiner—Samuel Barts

[57] ABSTRACT

Copper and vanadium catalyst components are recovered and dialkyl esters of dicarboxylic acids are synthesized by precipitating the catalyst metals with an alcohol selected from the group consisting of methanol, ethanol, and isopropanol removal of the precipitate, and then heating the mixture.

6 Claims, No Drawings

CATALYST RECOVERY AND DIALKYL ESTER SYNTHESIS

FIELD OF THE INVENTION

This invention relates to the treatment of a dewatered stream containing dicarboxylic acids, including glutaric acid, succinic acid, and adipic acid, as well as catalyst metal compounds of copper and vanadium to recover the catalyst metals and convert the dicarboxylic acids into dialkyl esters.

BACKGROUND OF THE INVENTION

In a commercial process for the manufacture of adipic acid, cyclohexanol and cyclohexanone are oxidized with nitric acid in the presence of copper and vanadium catalysts. The resulting product contains adipic acid, as well as glutaric acid, and succinic acid. Conventionally, most of the adipic acid is removed from the product by crystallization, and the remaining portion of the product has in the past been treated in various processes to recover other useful products and the copper and vanadium catalyst metals. For example in U.S. Pat. No. 4,375,552 to Kuceski the stream after crystallization and removal to most of the adipic acid is treated with an alcohol to form esters which are not soluble in the aqueous phase. The esters are then removed from the stream and the catalyst metals which remain in the aqueous phase are recycled to the nitric acid oxidation step. In U.S. Pat. No. 4,316,775 to Nash the stream after crystallization and removal of most of the adipic acid is treated with methanol to form the dimethylesters of the acids, the stream is then treated with an organic solvent which extracts the acid esters, and the aqueous phase is stripped of methanol, and the remainder, containing the catalyst metals is recycled to the nitric acid oxidation of cyclohexanol and cyclohexanone step.

SUMMARY OF THE INVENTION

The present invention is a process for the recovery of copper and vanadium components from a molten dewatered stream containing dicarboxylic acids, including glutaric acid, succinic acid, adipic acid, and copper and vanadium compounds, which comprises mixing methanol (or ethanol or isopropanol) with said stream at a temperature in the range of 40 to 140 degrees C. thereby precipitating copper glutarate and vanadium oxides, and separating the precipitate from the other remaining components.

The present invention is also a process for the production of dialkyl esters of dicarboxylic acids and the recovery of copper and vanadium components from a molten dewatered stream containing dicarboxylic acids including glutaric acid, succinic acid, adipic acid, and copper and vanadium compounds, which comprises mixing more than a stoichiometric amount of alcohol, usually methanol (based on the amount of alcohol necessary to convert the dicarboxylic acid content of the stream to diesters), with said stream at a temperature in the range of 40 to 140 degrees C. thereby precipitating copper glutarate and vanadium oxides, separating the precipitate from the remaining components, heating the remaining components to a temperature in the range of 150 to 220 degrees C. at a pressure of 1 to 5 atmospheres absolute, thus forming dialkyl esters of dicarboxylic acids, vaporizing the excess alcohol, diesters of dicarboxylic acid, and the water formed, and recovering the diesters of dicarboxylic acids. The term "dialkyl esters" means diesters of methanol, ethanol, or isopropanol.

The precipitated and separated copper glutarate and vanadium oxides may be dissolved in nitric acid and used catalytically in the nitric acid oxidation of cyclohexanol and cyclohexanone.

The amount of alcohol added to the molten dewatered stream will usually be on a weight basis at least equal to the weight of the stream, and preferably is 1.5 to 2.0 times the weight of the dewatered stream.

When alcohol is added to the molten dewatered stream, the temperature of the mixture will usually be in the range of about 60 to 110 degrees C.

DETAILED DESCRIPTION

Best Mode Contemplated

A molten mixture of dicarboxylic acids (adipic, glutaric, succinic, and some other organic acids) containing copper and vanadium compounds is obtained by dewatering an adipic acid manufacturing stream from which most of the adipic acid had been removed by crystallization. The molten mixture is mixed with methanol at a temperature in the range of 60 to 100 degrees C. Normally the amount of methanol is 1 to 2 pounds per pound of molten mixture. Copper glutarate and vanadium oxide solids form and become suspended in the solution of hot methanol containing the dissolved dicarboxylic acids. This slurry is filtered in a continuous fashion. The catalysts metal compounds form the filter cake which is moved to catalyst solution vessel, where it is dissolved in nitric acid, and may now be recycled to the nitric acid oxidation of cyclohexanol and cyclohexanone to adipic acid. The liquid (mostly methanol containing dissolved dicarboxylic acids) is moved to a reactor, where it is heated to a temperature in the range of 150 to 220 degrees C. at a pressure of 1 to 5 atmospheres absolute: preferably at a temperature in the range of 175 to 185 degrees C. and a pressure of 2 to 3 atmospheres absolute. This reactor may be, and preferably is, a circulating two phase reactor with vapor stripping. The feed rates and liquid level in the reactor is adjusted so that conversion of the dicarboxylic acids to esters is substantially complete, and dimethyl esters are removed overhead, along with methanol, and the water formed during esterification. Vapor product composition typically is 35% dimethyl esters, 3% monomethyl esters, 50% methanol, and 10% water. The overhead products are separated in condenser 5, and the methanol and monomethyl esters are recycled.

EXAMPLE 1

817 grams of a molten dewatered mixture of adipic acid, glutaric acid, succinic acid containing copper and vanadium catalyst metals were mixed with 1658 grams of methanol at a temperature of about 80 degrees C. and the product filtered. The solids were analyzed. The solids were mostly copper glutarate and vanadium oxides, with some succinic acid and adipic acid.

650 grams of the filtrate were charged to a liter stainless steel autoclave equipped with an agitator and heater.

The liquid was heated to 188 degrees C. (pressure about 400 pounds per square inch gauge), and the pressure was slowly released to 20 pounds per square inch gauge. The remaining filtrate was continuously pumped through the autoclave at a rate of 360 cc/hr. for about 5 hours. This portion of the filtrate entered the autoclave below the liquid level. The temperature was maintained at 188-190 degrees C. and at a pressure of 20 pounds per square inch gauge. Vapor was continuously removed, condensed, and analyzed. The vapor composition was approximately 30% dimethyl esters, 4.5% monomethyl esters, 10.5% water, and 55% methanol. About 50% of the dimethyl esters was dimethyl adipate, about 33% was dimethyl glutarate, and about 17% was dimethyl succinate.

EXAMPLE 2

600 grams of methanol were heated to 70 degrees C. with 400 grams of a dewatered mixture of succinic acid, glutaric acid, adipic acid, copper and vanadium catalysts, plus traces of nitric acid and water obtained from a commercial adipic acid plant. (The readily recoverable adipic acid had been removed from the 400 gram mixture.) The 1000 gram mixture was stirred and then filtered. Approximately 10 grams of blue solids were recovered and analyzed. The analysis showed that the mixture was about 25% copper salts, 3% vanadium oxides, and 50% glutaric acid.

Succinic acid and adipic acid were also present in the solids. The solids can be dissolved in dilute nitric acid and recycled to the step of nitric acid oxidization of cyclohexanol and cyclohexanone. At least 80% of the catalyst was recovered. The filtrate can be esterified by the process of Example 1.

What is claimed is:

1. A process for the recovery of copper and vanadium components from a molten dewatered stream containing dicarboxylic acids, including glutaric acid, succinic acid, adipic acid, and copper and vanadium compounds, which comprises mixing an alcohol selected from the group consisting of methanol, ethanol, and isopropanol with said stream at a temperature in the range of 40 to 140 degrees C. thereby precipitating copper glutarate and vanadium oxides, and separating the precipitate from the other remaining components.

2. A process for the production of dialkyl esters of dicarboxylic acids and the recovery of copper and vanadium components from a molten dewatered stream containing dicarboxylic acids including glutaric acid, succinic acid, adipic acid, and copper and vanadium compounds, which comprises mixing more than a stoichiometric amount of an alcohol selected from the group consisting of methanol, ethanol, and isopropanol (based on the amount of alcohol necessary to convert the dicarboxylic acid content of the stream to diesters) with said stream at a temperature in the range of 40 to 140 degrees C. thereby precipitating copper glutarate and vanadium oxides, separating the precipitate from the remaining components, heating the remaining components to a temperature in the range of 150 to 220 degrees C. at a pressure of 1 to 5 atmospheres absolute, thus forming dialkyl esters of dicarboxylic acids, vaporizing the excess alcohol, diesters of dicarboxylic acid, and the water formed, and recovering the diesters of dicarboxylic acids.

3. The process of claim 1 in which the precipitate of copper glutarate and vanadium oxides is dissolved in nitric acid and used catalytically in the nitric acid oxidation of cyclohexanol and cyclohexanone.

4. The process of claim 2 in which methanol is added to the molten dewatered stream in an amount on a weight basis at least equal to the weight of the stream.

5. The process of claim 4 in which the methanol is added to the molten dewatered stream in an amount on a weight bases 1.5 to 2.0 times the weight of the dewatered stream.

6. The process of claim 1 in which the temperature is in the range of 60 to 110 degrees C.

* * * * *